United States Patent [19]
Elmaleh

[11] Patent Number: 5,890,492
[45] Date of Patent: *Apr. 6, 1999

[54] SYSTEM FOR CONTROLLING THE SPREAD OF HIV/AIDS AND OTHER INFECTIOUS DISEASES

[76] Inventor: David R. Elmaleh, 85 E. India Row, Boston, Mass. 02110

[ * ] Notice: This patent issued on a continued prosecution application filed under 37 CFR 1.53(d), and is subject to the twenty year patent term provisions of 35 U.S.C. 154(a)(2).

[21] Appl. No.: 475,363

[22] Filed: Jun. 7, 1995

[51] Int. Cl.$^6$ ...................................................... A61B 19/00
[52] U.S. Cl. .............................................................. 128/897
[58] Field of Search ........................................ 128/897–98

[56] References Cited

U.S. PATENT DOCUMENTS 4,860,767   8/1989   Hatsuwi .
5,193,541   3/1993   Maekawa .

OTHER PUBLICATIONS

Berrios et al. "HIV Antibody Testing Among Those at Risk for Infection," *Journal of the American Medical Association*, vol. 270, No. 13, pp. 1576–1580 (1993).
*HIV/AIDS Surveillance Report*, Second Quarter Edition, vol. 5, No. 2, Jul. 1993.
Jasny, "AIDS 1993: Unanswered Questions," *Science*, vol. 260, p. 1219,(1993).
Merson, "Slowing the Spread of HIV: Agenda for the 1990s," *Science*, vol. 260, pp. 1266–1278(1993).
Baunn, "Progress Fitful on Understanding AIDS, Developing Therapies," *C&EN*, pp. 26–31, (Aug. 24, 1994).
Cohen, "Somber News From the AIDs Front," *Science*, vol. 260, pp. 1712–1713(18 Jun. 1993).
Aldhous, "French Venture Where U.S. Fears to Tread" *Science*, vol. 257, p. 25 (3 Jul. 1992).
Catania et al. "Prevalence of AIDS–Related Risk Factors and Condom Use in the United States," *Science*, vol. 258, pp. 1101–1106(13 Nov. 1992).
Haynes, "Scientific and Social Issues of Human Immunodeficiency Virus Vaccine Development," *Science*, vol. 260, pp. 1279–1285(28 May 1993).

*Primary Examiner*—John P. Lacyk
*Attorney, Agent, or Firm*—Fish & Richardson P.C.

[57] ABSTRACT

A method for controlling the spread of HIV/AIDS and other infectious diseases. Individuals desirous of reducing the risks of infection and preventing the spread of such diseases voluntarily participate in a testing program whereby regular periodic screening tests are performed to indicate the infection status of each such individual for any of several infectious diseases. The infection status information is coded for each individual and is stored in a confidential database. An individual can access his infection status information upon making an inquiry using a unique personal identification number, or PIN. The individual's identification information is matched with his infection status information in the database and provides that information immediately either orally or in written form. Two participating members of the program can obtain their infection status data jointly, thereby providing reliable, current infection status information to each other contemporaneously while avoiding the risks of nondisclosure or misrepresentation of such information by one or both parties.

16 Claims, 2 Drawing Sheets

XXXX GROUP

INFECTION STATUS
REPORT

| MEMBER 1 | MEMBER 2 |
|---|---|
| *HIV | *HIV |
| T: 1/5/95 N | T: 1/27/95 N |
| T: 6/1/95 N | T: 6/7/95 N |

--------► CAUTION ◄---------

INFECTION RISK MEMBER 2!

PLEASE REFRAIN FROM HIGH-RISK
BEHAVIORS WITH NONINFECTED
INDIVIDUALS. CALL DIRECTOR AT
(617) 555-0070 FOR INFORMATION

PRINT REPORT?            Y OR N

FIG. 2

SYSTEM FOR CONTROLLING THE SPREAD OF HIV/AIDS AND OTHER INFECTIOUS DISEASES

TECHNICAL FIELD

The present invention relates to methods for preventing the spread of infectious diseases which are transmissible among humans through contact with body fluids, and more particularly to methods for preventing the spread of HIV/AIDS and other venereal, or sexually transmissible, diseases.

The term "HIV/AIDS", as used herein, refers to acquired immune deficiency syndrome (AIDS), believed to be caused by the human immunodeficiency virus (HIV).

BACKGROUND OF THE INVENTION

The existence of sexually transmissible diseases is a reality of the human condition. Infectious diseases such as hepatitis, and venereal diseases such as gonorrhea, syphilis, chlamydia and herpes, have not yet been eradicated, although they are currently treatable if properly diagnosed. Other sexually transmissible diseases, such as HIV/AIDS and certain strains of hepatitis, are virulent and continue to spread worldwide. Although much work is currently being done in the area of HIV/AIDS research, there is so far no cure, no vaccine, and no effective long-term treatment for the disease.

Current knowledge does not even extend to an understanding of all the mechanisms by which HIV/AIDS is transmitted. It is known, however, that certain high-risk behaviors render one more susceptible to infection with HIV. These high-risk behaviors include, but are not limited to, promiscuity, unprotected sex, homosexual sex, drug use, sex with drug users, and the sharing of hypodermic syringes and needles. Identification of high-risk behaviors and individuals tending to engage in such behaviors, and education of those individuals about the risks inherent in their activities, is an important step in reducing the incidence of HIV infection in the general population. Behavior modification is thus a critical goal in the war against the spread of HIV/AIDS and other sexually transmissible diseases for which no cure or suitable treatment is known.

It is an object of the present invention to provide a method for preventing the spread of sexually transmissible diseases, principally through behavior modification, particularly among individuals engaging in potentially high-risk behaviors.

It is another object of the present invention to provide a method for preventing the spread of infectious diseases by providing an easily-accessible information database which contains updated infection status information about individuals who participate in a regular screening program to test for infection and who wish to minimize the risks of becoming infected.

SUMMARY OF THE INVENTION

The method of the present invention accomplishes these and other objectives, in one aspect, by a method for controlling the spread of HIV/AIDS and other infectious diseases. According to the practice of the present invention, a group of persons who are desirous of reducing the risk of infection with such diseases is identified. Members of the group are periodically tested for seropositive reactions to any one or more of a number of identifiable infectious diseases, including syphilis, gonorrhea, chlamydia, herpes, hepatitis and HIV/AIDS. The test information for each person forms a body of infection status data which is coded uniquely for each member of the group and is stored in a confidential database. The infection status data for a member of the group can be accessed by that member only in response to an inquiry which includes that member's unique identification code.

The infection status data for any member of the group includes identifying information about the requesting member or members and a unique personal identification number, or PIN. Identification of the tests performed on the member includes, for example, the dates of such tests, the results of each test, the infection status of the member as of the most recent test date, and statistical information about various infectious diseases. Other pertinent information about the requesting member(s) may also be included. The infection status data can be provided in oral or written form to the requesting member(s).

Testing for the presence of infectious diseases is performed at regular intervals, such as semiannually. The testing process can include blood tests or other specific tests which identify diseases such as HIV/AIDS, syphilis, gonorrhea, chlamydia, herpes, hepatitis and the like.

The confidential database of infection status data is easily accessible through electronically coded inquiry means, which can be, for example, a bar-coded or magnetically recorded identification label. Once the database is accessed by a member upon input of a member identification code, information on the member's infection status can be accessed upon input of a member's PIN.

A confirmed member of the identified group can inquire about his or her infection status confidentially and can do so individually or in conjunction with an inquiry from another member of the group. All that is required is that the inquiring members have an identification code which can be used to access the information from the database, and a PIN which accesses the member's individual databank in the database.

These and other features of the invention will be more fully appreciated with reference to the following detailed description.

BRIEF DESCRIPTION OF THE DRAWINGS

FIG. 2 is an illustration of a typical infection status report for two individuals according to the method of the invention.

DETAILED DESCRIPTION OF THE INVENTION

Figure 1:
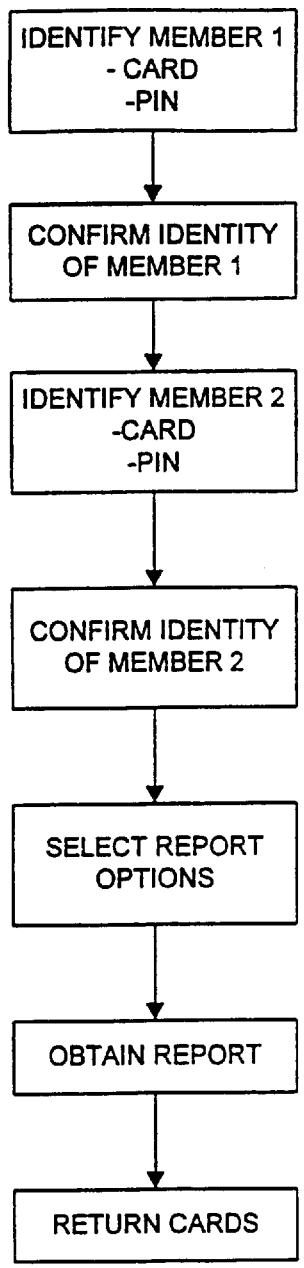
FIG. 1 is a schematic illustration of a sequence of steps for obtaining infection status data according to the method of the invention.

The method of the present invention is based on voluntary participation of individuals in a program which is designed, at least in part, to reduce the spread of infectious diseases including HIV/AIDS and other sexually transmissible diseases. This goal is accomplished by acquiring and making readily available, on a confidential basis, current, reliable infection test information about a participant. It is contemplated that this information could be accessed by that participant from virtually anywhere at any time of day or night, using available technology.

It is anticipated that participants in such a program will enjoy a number of benefits, both short-term and long-term, including:

a. reduced occurrence of infection by infectious diseases from persons within the group and ultimately, from persons in the general population outside the group;

b. improved and more open communications between participants about the infection status of participants;

c. reduced anxiety and fear attributable to unknown risks of disease transmission and infection among participants in the group;

d. potentially substantial health cost savings, including reduced individual health insurance costs;

e. improved health habits;

f. awareness and minimization of high-risk behaviors without necessarily having to refrain from sexual activities;

g. increased awareness of the impact of behavior modification on the spread of infectious diseases; and h. substantially greater physical health and comfort by avoidance of treatments for infectious diseases.

The first step in the method of the present invention is to identify a group of individuals who are interested in voluntarily reducing their chances of unknowingly transmitting or being infected with an infectious disease.

Each member of the group is issued an identification card, badge or pin which identifies him as a participating member of the group. The card or badge can bear a logo indicating the name of the group or association and can include an identification code in alphanumeric, bar-code or magnetic-strip format. This identification code identifies the bearer of his status as a member of the group, just as a bank's identification card identifies the bearer as a customer of that bank. Each member of the group will also be assigned or asked to select a unique personal identification number, or PIN, such as a multi-digit numeric or alphanumeric sequence. If desired, the individual's social security number can serve as his PIN. The PIN is used to access the individual's test information and infection status data in the database. Once identified as a participating member of the group, the member is eligible to receive group member benefits, such as specialized mailings targeted to like-minded individuals, and discounts on health and fitness activities, supplies, social activities, health insurance, and the like.

Each individual of the group agrees to participate in regular, periodic medical testing to screen for the presence of any number of infectious diseases. Testing is performed by authorized health care practitioners in an appropriate clinical environment, in much the same manner as testing is done in a health maintenance organization. The test information for an individual is coded with his or her PIN, and all health test information relating to an individual identified with a particular PIN is stored together in the confidential database. Information relating to an individual's infection status is accessible to members of the group according to specified procedures which will be more fully detailed below. The confidential database is accessible via any known means for accessing such electronically coded and stored information, including through on-line computer network services, such as, for example, the Internet.

The infection status data for each member of the group is provided to that member in response to an authorized inquiry from that member. The authorized inquiry consists of an input which includes the individual's identification code and PIN. In a preferred practice, a member of the group makes an inquiry about his infection status by inserting his or her identification card into a bar-code or magnetic strip reading device, such as those used in automatic banking kiosks, grocery stores and the like, or by entering his identification code into an electronic keypad, which is electronically linked to means for accessing the database.

The individual's identification code is processed and the identity of the individual as a member of the participating group is confirmed. The individual is then asked to input his PIN in order to access his personal infection status information. A report menu is presented to the individual, who must then indicate the disease or diseases for which infection status information is requested. The database program then provides the individual's requested infection status data to the individual, preferably in the form of a printed report which is printed immediately from an associated printer on site.

The individual's infection status data can alternatively be provided in oral form in response to a telephone inquiry, in which the individual's identification code is orally or electronically transmitted through the telephone lines to a live operator or to a device which is capable of receiving the information and processing it according to known procedures. The identity of the individual as a participating member of the group is confirmed, and the individual's PIN is requested as described above. The individual inputs his PIN via the telephone keypad, and the database is searched for test information which is coded with the individual's PIN. The test information matching the individual's PIN is accessed and can be read by a voice synthesizer or a live operator over the telephone to the individual.

Confidentiality is maintained because the individual's name and address are never used to access the test information and are not printed on the individual's identification card.

FIG. 1 illustrates a sequence of steps in a preferred embodiment of the invention, in which two participating members can obtain contemporaneous infection status information about each other. Member No. 1 identifies himself as a participant in the group by presenting his identification card to a card-reading device, such as those used in automated teller machines (ATMs). Member No. 1 is asked to provide his unique personal identification number, or PIN, which he inputs via an electronic keypad, a voice recognition system, or other known technology. The identify of Member No. 1 as a participant in the system is confirmed, and his infection test data is accessed in the database. Member No. 2 is then prompted to identify herself in the same manner and is confirmed as a participant as previously described. Once the identities of the two requesting members are confirmed and their respective infection status databanks are accessed, the members are queried about the test information they want. The members can typically select from a menu of options ranging from "HIV only" to "All of the above", in which test status information for all tests performed is provided. The members select the desired test status information and obtain a test status report, illustrated in FIG. 2. The members are then queried about whether a writer report is desired. If so, a printer on-site generates the report, and the members' cards are returned to the members after the report is printed and removed. The display screen which prompts the members is then erased so that a subsequent user does not see the previous user's infection status report. If no written report is requested, the members' cards are returned to the members and the display screen is erased.

FIG. 2 also illustrates a typical precautionary message that is included in the report in the event that one or more test results is positive for the disease or virus tested. For example, Member No. 2 shows a positive test for HIV on Jun. 7, 1995. Member No. 1 shows negative tests for HIV for the last two tests performed. The goal of the method described herein is prevention of infection, and the precautionary messages, if used, should be appropriately worded.

No further information about an infected individual will be provided, and it is the responsibility of the members requesting and receiving infection status information about one another to use the information appropriately and constructively.

The confidential database is designed to be accessed by all members of the group. However, to protect an individual's privacy, only he or someone in possession of his unique PIN can request his infection status information. Confidentiality of the infection status information is maintained and assured by providing an individual's infection status only to the individual to whom it pertains, and only if that individual identifies himself as a member of the group by providing his unique PIN.

Because an individual's PIN is unique to an individual, it is intended to be kept confidential by that individual and is not publicly known or available. Of course, if a member loses or forgets his PIN, or its confidentiality becomes compromised, a new PIN can be assigned to, or selected by, the individual.

All persons who are interested in reducing their risk of transmitting or being infected with an infectious disease are encouraged to participate in the system outlined herein, regardless of their infection status. For example, HIV-positive individuals may wish to participate in the system described herein so that they can develop intimate relationships only with other HIV-positive individuals, thereby reducing the involuntary spread of HIV/AIDS to noninfected individuals. Furthermore, a participating member who tests negative for HIV/AIDS has the ability to know the infection status of any potential partner who is also a participant in the system, before he engages in an intimate relationship or other potentially high-risk behaviors with that partner. Finally, the provision of a conspicuous means for identifying an individual as a participating member of the group, in the form of a pin or other logo-bearing insignia or tag, facilitates open communications between individuals and reduces the risks of infection and disease transmission through nondisclosure of infection status information.

Individuals who have not been tested will also be permitted to access the database to obtain information about their infection status. For example, a message indicating that the individual is interested and is therefore believed to be "at risk" due to failure to complete testing may be included in his infection status report, to alert potential partners to his high-risk status. Alternatively, untested individuals could be prohibited from accessing the database until and unless they have been tested according to the schedules recommended by the group.

Practice of the method of the invention does not guarantee that participants will remain free of infection. However, the risks of infection associated with spontaneous intimate relationships and other high-risk behaviors can be significantly reduced, thereby ensuring greater safety and protection from infectious diseases for all members of the group and ultimately for members of the general population. The result is expected to be a reduction in the spread of HIV/AIDS and other infectious diseases.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A method for controlling the spread of HIV/AIDS and other infectious diseases selected from the group consisting of HIV/AIDS, syphilis, gonorrhea, chlamydia, herpes, and hepatitis, said method comprising the steps of:

A. identifying a group of persons desirous of reducing their risk of infection with said diseases, B. periodically testing said persons in said group for infection with any of said infectious diseases to obtain infection status data for each person, C. storing said infection status data for each person in a confidential database, wherein said infection status data for each person is coded uniquely for each said person, D. providing selected infection status data about a member of said group contemporaneously to a plurality of requesting members in response to an authorized inquiry from said members.

2. The method of claim 1 wherein each member of said group is identified with a unique personal identification number.

3. The method of claim 1 wherein said infection status data for a member of said group includes information about at least one of the following:

a. said unique identification code for said member as a member of said group, b. said unique personal identification number for said member, c. identification of tests performed on said member, d. dates of said tests, e. results of said tests, f. an infection status of said member as of said dates of said tests, g. the most recent test date, h. identification of tests performed on said most recent test date, i. results of said tests performed on said most recent test date, j. the infection status of said member as of said most recent test date, k. statistical information on sexually transmissible diseases; and l. behavioral recommendations based on said infection status of said member.

4. The method of claim 1 comprising the further step of testing said members semiannually.

5. The method of claim 1 comprising the further step of providing said infection status data of said requesting members in written form.

6. The method of claim 1 comprising the further step of providing said infection status data of said requesting members in oral form.

7. The method of claim 1 comprising the further step of electronically accessing said confidential database through coded inquiry means.

8. The method of claim 7 wherein said coded inquiry means comprises a bar-coded identification label.

9. The method of claim 7 wherein said coded inquiry means comprises a magnetically recorded identification label.

10. The method of claim 7 wherein said coded inquiry means comprises an alphanumeric identification code.

11. The method of claim 1 wherein said authorized inquiry comprises information identifying said members as members of said group and a personal identification number unique to each of said members for accessing said infection status information for said members.

12. A system for storing and controlled retrieval and sharing of infection status data pertaining to individuals who are part of a consensual group, the infection status of an individual in the group indicating whether that individual has undergone a test for at least one infectious disease selected from the group consisting of HIV/AIDS, syphilis, gonorrhea, chlamydia, herpes, and hepatitis, and, if so the outcome and date of that test, the system comprising:

a) electronic data storage comprising: i) stored infection status data pertaining to multiple individuals each of whom is a member of the consensual group;

b) access control to data in the electronic data storage permitting a first individual who is a member of the consensual group to obtain infection status data of a second individual who is a member of the consensual group, said access control comprising a block preventing individuals not a member of the consensual group from gaining access to infection status data of members of the group.

13. The system of claim 12 in which the access control comprises a remote terminal connected to the data storage which permits a user to enter alphameric information for interaction with the block to determine whether to transmit infection status data to the terminal and, if so, which infection status data to transmit to the terminal, based on a entry of information at the terminal establishing that the user is a member of the consensual group.

14. A system for storing and controlled retrieval and sharing of infection status data pertaining to individuals who are organized into consensual groups, the infection status of an individual in one of the groups indicating whether that individual has been tested for at least one infectious disease selected from the group consisting of HIV/AIDS; syphilis, gonorrhea, chlamydia, herpes, and hepatitis, and, if so the outcome and date of that test, the system comprising:

a) electronic data storage comprising: i) stored infection status data pertaining to multiple participating individuals who are organized into multiple consensual groups;

b) access control to data in the electronic data storage permitting a first individual who is a member of a first consensual group but not of a second consensual group to obtain infection status data of a second individual who is a member of the first consensual group, said access control comprising a block preventing the first individual from gaining access to infection status data for individuals who are members of the second consensual group but not the first consensual group.

15. The system of claim 14 in which the block further preventing the first individual from obtaining access to any information in the data storage if the data storage does not contain infection status data of the first individual.

16. The system of claim 14 in which the access control comprises a remote terminal connected to the data storage which permits a user to enter alphameric information for interaction with the block to determine whether to transmit infection status data to the terminal and, if so, which infection status data to transmit to the terminal, based on a entry of information at the terminal establishing that the user is a member of at least one consensual group and that the user's infection status data is in the data storage.

* * * * *